(12) United States Patent
Welchel et al.

(10) Patent No.: US 7,771,043 B2
(45) Date of Patent: Aug. 10, 2010

(54) EYEWEAR WITH ENHANCED AIR FLOW AND/OR ABSORPTION FEATURES

(75) Inventors: Debra N. Welchel, Woodstock, GA (US); Megan Christine Hansen Smith, Roswell, GA (US); Matrice B. Jackson, Woodstock, GA (US); Andrew J. Beltz, Neenah, WI (US); Russell J. Kroll, Atlanta, GA (US); Philip D. Palermo, Marietta, GA (US); Mark D. Londborg, Atlanta, GA (US); Suzuko Hisata, Atlanta, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 12/263,810

(22) Filed: Nov. 3, 2008

(65) Prior Publication Data

US 2009/0077722 A1     Mar. 26, 2009

Related U.S. Application Data

(62) Division of application No. 11/413,517, filed on Apr. 28, 2006, now abandoned.

(51) Int. Cl.
G02C 5/00 (2006.01)
(52) U.S. Cl. .......................................... 351/41
(58) Field of Classification Search .................. 351/62, 351/41
See application file for complete search history.

(56) References Cited

U.S. PATENT DOCUMENTS

| | | | |
|---|---|---|---|
| 182,013 A | 9/1876 | Andross | |
| 1,026,272 A | 5/1912 | Leveque | |
| 1,562,350 A | 11/1925 | Luckey | |
| 3,038,376 A * | 6/1962 | Kancepolsky | 351/157 |
| 3,133,982 A * | 5/1964 | Janz | 351/62 |
| 3,160,735 A | 12/1964 | Aufricht | |
| 3,377,626 A | 4/1968 | Smith | |
| 4,209,234 A | 6/1980 | McCooeye | |
| 4,250,577 A | 2/1981 | Smith | |
| 4,419,993 A | 12/1983 | Petersen | |
| 4,638,728 A | 1/1987 | Elenewski | |
| 4,796,621 A | 1/1989 | Barle et al. | |

(Continued)

FOREIGN PATENT DOCUMENTS

DE      3323670      1/1985

(Continued)

OTHER PUBLICATIONS

Patent Abstracts of Japan, JP 2005215324, Publication Date: Aug. 11, 2005.

(Continued)

Primary Examiner—Ricky L Mack
Assistant Examiner—Vipin M Patel
(74) Attorney, Agent, or Firm—Nathan P. Hendon

(57) ABSTRACT

Eyewear having an enhanced air flow and/or absorption features which may be used for safety, sports, and the like. The eyewear may desirably provides features in design and/or function of the structure to enhance air flow and reduce moisture. Additional elements such as removable pads and/or cartridges may be used with the eyewear to enhanced airflow and reduce moisture adjacent a user's eyes and face as well.

6 Claims, 5 Drawing Sheets

U.S. PATENT DOCUMENTS

| | | | |
|---|---|---|---|
| 4,799,782 A | | 1/1989 | Tuttle |
| 4,824,233 A | * | 4/1989 | Jannard .................... 351/47 |
| 4,863,257 A | | 9/1989 | Morgan |
| 4,868,929 A | | 9/1989 | Curcio |
| 4,934,807 A | * | 6/1990 | Bolle et al. ................. 351/62 |
| 4,937,880 A | | 7/1990 | Beard |
| 4,942,626 A | | 7/1990 | Stern et al. |
| 4,942,629 A | | 7/1990 | Stadlmann |
| 5,107,543 A | | 4/1992 | Hansen |
| 5,162,823 A | | 11/1992 | Goldstein |
| 5,191,364 A | | 3/1993 | Kopfer |
| 5,319,397 A | | 6/1994 | Ryden |
| 5,351,339 A | | 10/1994 | Reuber et al. |
| 5,363,153 A | | 11/1994 | Bailiff |
| 5,363,512 A | | 11/1994 | Grabos, Jr. et al. |
| 5,416,536 A | | 5/1995 | Tee, Jr. |
| 5,457,505 A | | 10/1995 | Canavan et al. |
| 5,459,533 A | | 10/1995 | McCooeye et al. |
| 5,517,700 A | | 5/1996 | Hoffman |
| 5,584,078 A | | 12/1996 | Saboory |
| 5,610,669 A | | 3/1997 | Kuipers et al. |
| 5,638,145 A | * | 6/1997 | Jannard et al. ............. 351/62 |
| 5,652,637 A | | 7/1997 | Marini |
| 5,720,281 A | | 2/1998 | Allen et al. |
| 5,898,468 A | | 4/1999 | Mage |
| 5,907,385 A | | 5/1999 | Flores et al. |
| 5,956,117 A | * | 9/1999 | Suh et al. .................. 351/156 |
| 5,956,119 A | | 9/1999 | Gibbs |
| 5,969,787 A | | 10/1999 | Hall et al. |
| 6,094,751 A | | 8/2000 | Parks |
| 6,318,369 B1 | | 11/2001 | Gregory |
| 6,637,038 B1 | | 10/2003 | Hussey |
| 6,701,537 B1 | | 3/2004 | Stamp |
| 6,783,235 B1 | | 8/2004 | Lin |
| 6,959,988 B1 | | 11/2005 | Sheldon |
| 7,077,137 B2 | | 7/2006 | Russell |
| 7,175,274 B1 | | 2/2007 | Markson |
| 7,372,646 B2 | | 5/2008 | Spivey |
| 7,448,749 B2 | * | 11/2008 | Tu .............................. 351/62 |
| 2003/0035082 A1 | | 2/2003 | Olney |
| 2004/0066486 A1 | | 4/2004 | Yi |
| 2004/0069302 A1 | | 4/2004 | Wilson et al. |
| 2004/0100384 A1 | | 5/2004 | Chen et al. |
| 2004/0107483 A1 | | 6/2004 | Thorson |
| 2004/0125334 A1 | | 7/2004 | Olney |
| 2005/0012893 A1 | | 1/2005 | Yamamoto |
| 2005/0160521 A1 | | 7/2005 | Hussey |
| 2005/0174470 A1 | | 8/2005 | Yamasaki |
| 2005/0225715 A1 | * | 10/2005 | Kopfer ....................... 351/62 |
| 2005/0227269 A1 | * | 10/2005 | Lloyd et al. ................. 435/6 |
| 2005/0237477 A1 | | 10/2005 | Lindahl |
| 2005/0270478 A1 | | 12/2005 | Curci et al. |
| 2005/0286734 A1 | | 12/2005 | Wang |
| 2006/0001827 A1 | | 1/2006 | Howell et al. |
| 2006/0126008 A1 | * | 6/2006 | Olney ......................... 351/62 |
| 2006/0197906 A1 | | 9/2006 | Goodis |

FOREIGN PATENT DOCUMENTS

| | | |
|---|---|---|
| GB | 264280 | 1/1927 |
| GB | 489530 | 7/1938 |
| GB | 2362472 | 11/2001 |
| WO | WO 97/04837 | 2/1997 |
| WO | WO 97/50013 | 12/1997 |
| WO | WO 98/39682 | 9/1998 |
| WO | WO 99/55180 | 11/1999 |
| WO | WO 02/02039 | 1/2002 |
| WO | WO 2004/098715 | 11/2004 |

OTHER PUBLICATIONS

Patent Abstracts of Japan, JP 2005269572, Publication Date Sep. 29, 2005.

\* cited by examiner

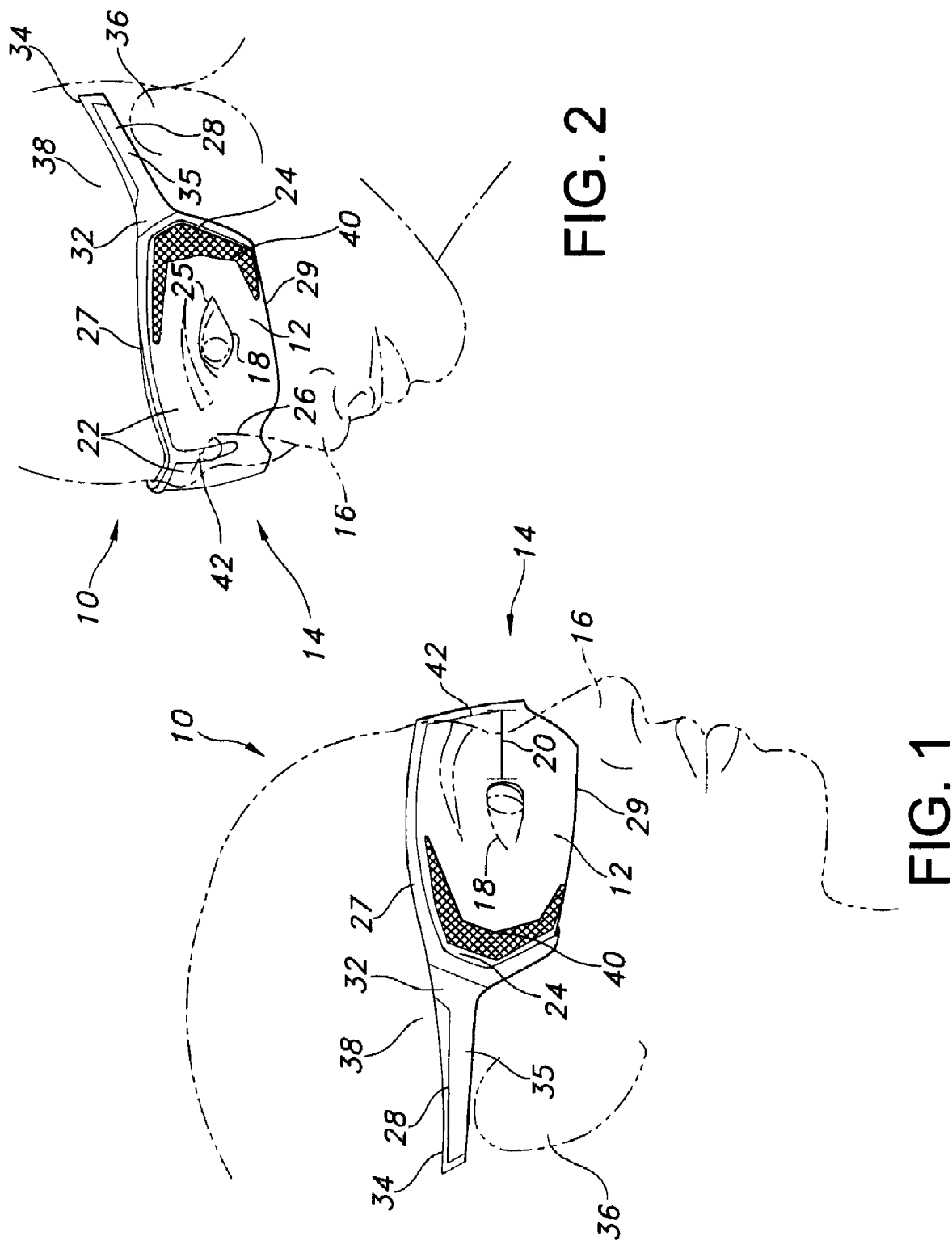

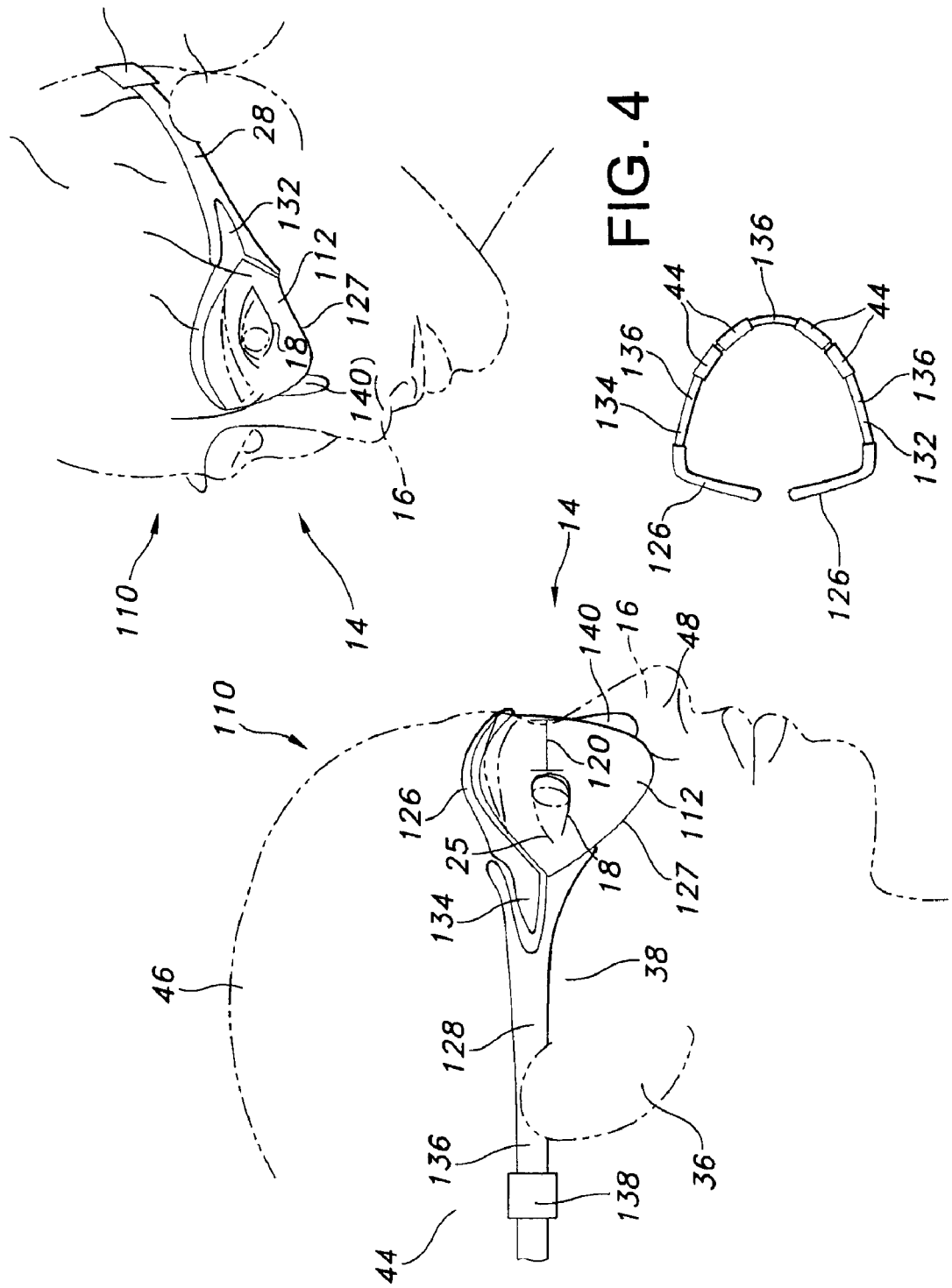

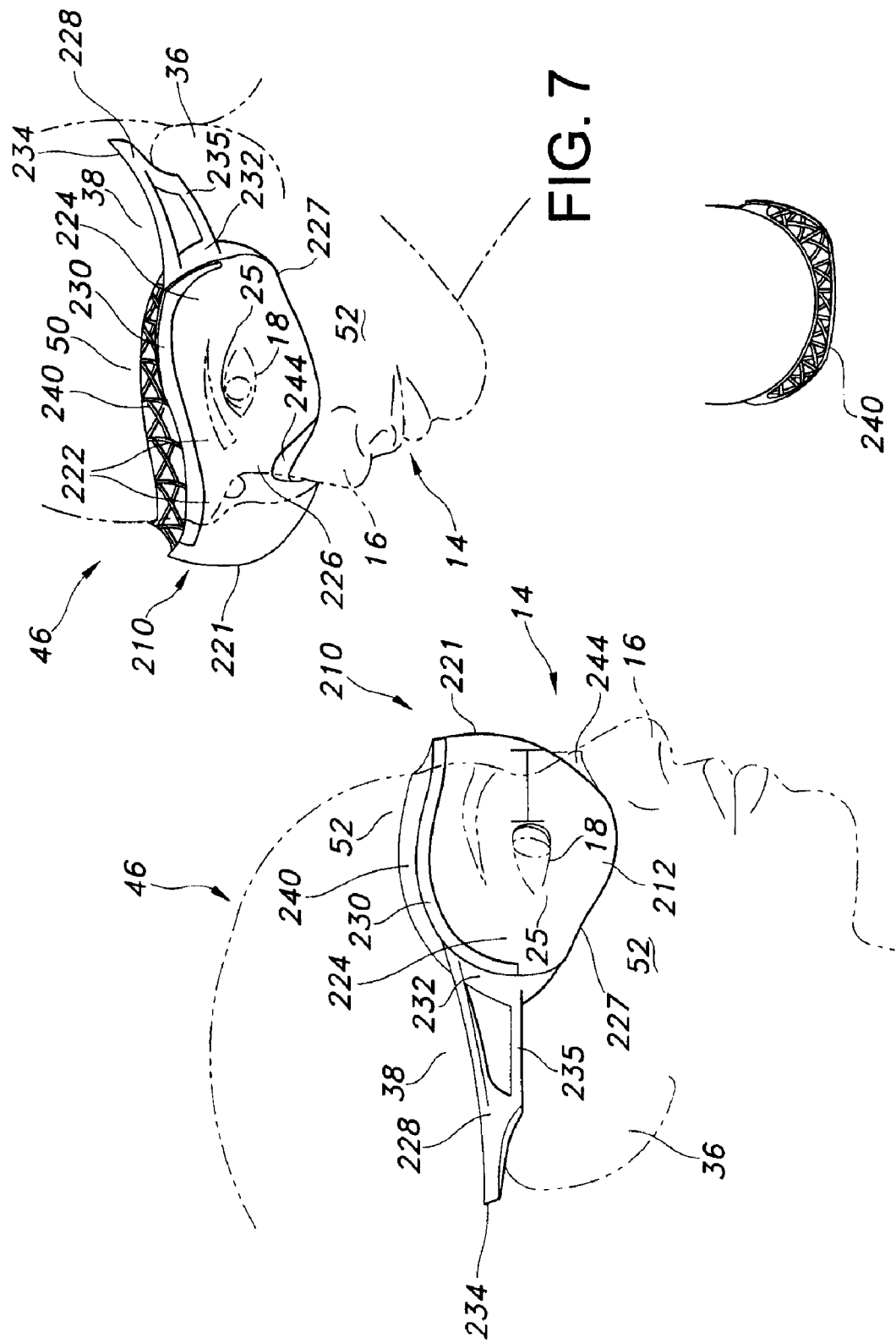

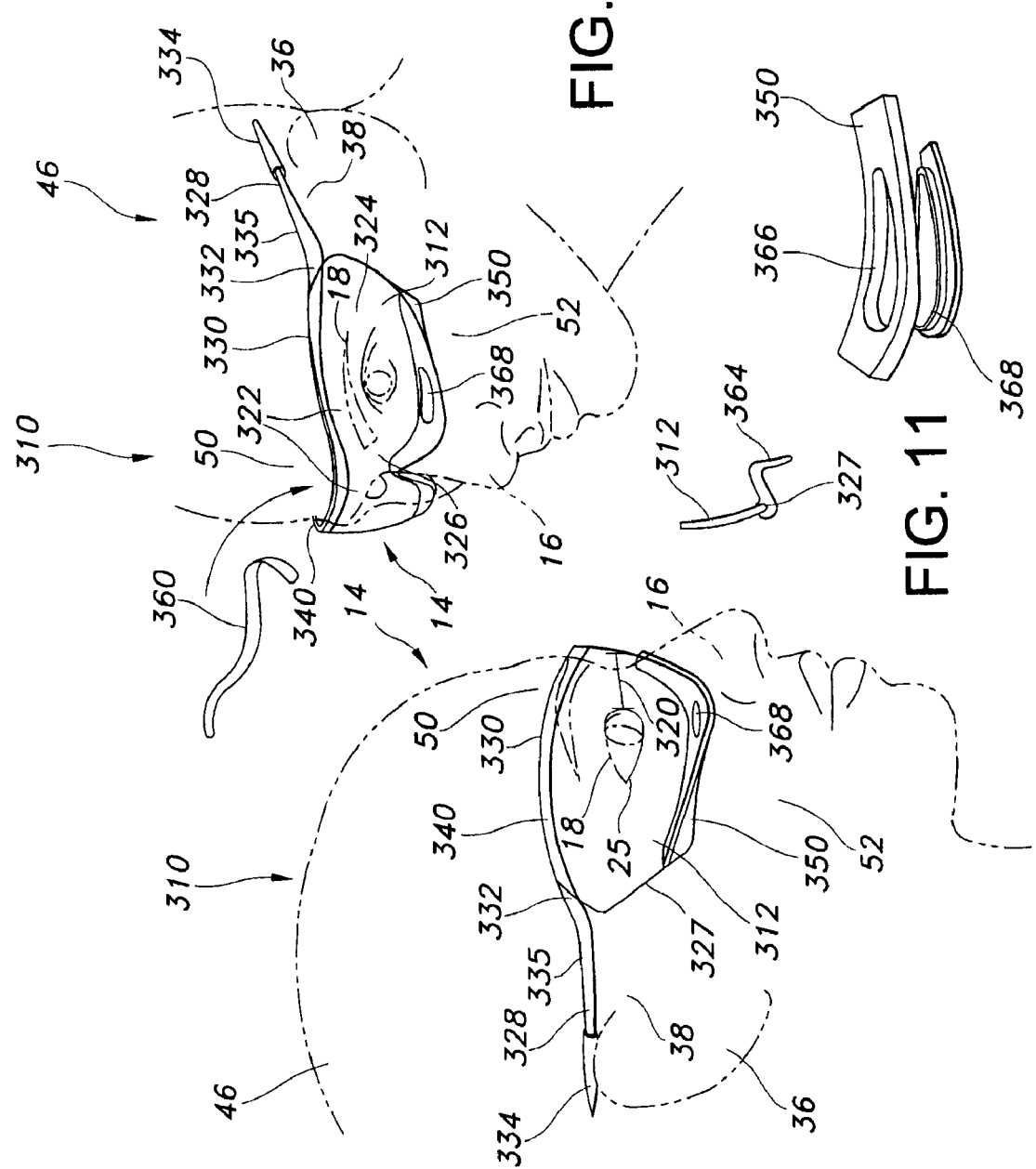

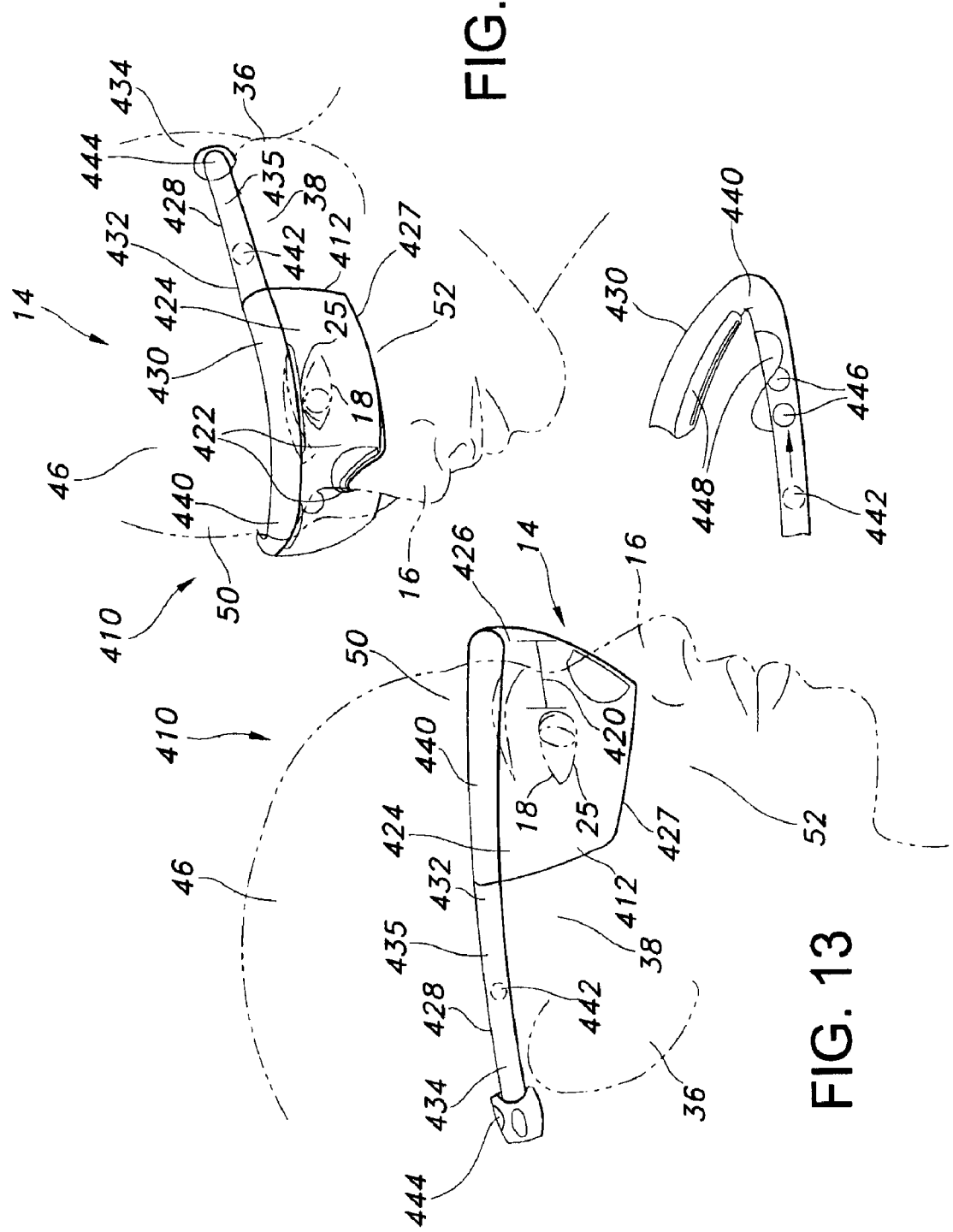

EYEWEAR WITH ENHANCED AIR FLOW AND/OR ABSORPTION FEATURES

This application is a Divisional of U.S. patent application Ser. No. 11/413,517, filed Apr. 28, 2006, now abandoned which is incorporated by reference herein.

BACKGROUND OF THE INVENTION

This invention relates to eyewear, and especially eyewear used for safety and/or activities such as sports.

Eyewear for safety applications in industrial use and/or sports are used to protect a user's eyes. Such eyewear is usually designed to fit relatively closely to a user's face, so that noxious gas, liquid, particles, contaminants, and the like, do not touch or affect a user's eye(s).

Safety and some sports glasses or eyewear are often designed and formed such that they are bulky and heavy to wear. Some are tight-fitting and uncomfortable as well, such as goggles or masks. In addition, such eyewear is often provided as in only a few sizes which do not fit every user's face well. Further, such eyewear suffers from the lack of appropriate ventilation, resulting in moisture build-up and fogging of the lenses. Such moisture build-up may interfere with vision as well as comfort. This results in poor compliance in users donning and wearing the eye wear. Moreover, eyewear which does not dissipate moisture may actually make it more difficult for a user to see when wearing the eyewear.

Therefore, safety and/or sports eyewear which is lightweight, adjustable and provides enhanced air flow and dissipates moisture in and around a user's eyes and face would be desirable. Such eyewear desirably provides protection for a user's eyes while providing design features which makes the eyewear more attractive to wear.

DEFINITIONS

As used herein, the term "glasses" or "eyewear" refers to eyeglasses, goggles, or other objects worn over the eyes.

As used herein, the terms "ear piece" or "ear pieces" refers to The portion of glasses or eyewear which extends from a lens and/or frame to extend over and/or about a portion of a user's ear to assist in holding the glasses or eyewear on a user's head.

As used herein, the phrase "custom fit" refers to an item that is provided or made in a proper size, shape and fit for the individual, particularly, to fit the contours of a certain area of an individual's body (For example, "These shoes were made to fit my feet very well.").

As used herein, the term "contour" refers to at least a portion of an item which is shaped to fit the outline or form of something (Example, "A contour sheet").

As used herein, the term "hinge" or "hinges" refers to a jointed or flexible device that connects and permits pivoting or turning of a part to a stationary component. Hinges include, but are not limited to, metal pivotable connectors, such as those used to fasten a door to frame, and living hinges. Living hinges may be constructed from plastic and formed integrally between two members. A living hinge permits pivotable movement of one member in relation to another connected member.

As used herein, the terms "contaminate", "contaminant" and/or "contamination" mean to make unclean or impure by contact. Such contact may be by liquid, solid and/or gas. For example, but not by way of limitation, mud that befouls shoes; noxious fumes that foul the air; bodily fluids that foul clean diapers.

As used herein, the term "fasteners" means devices that fasten, join, connect, secure, hold, or clamp components together. Fasteners include, but are not limited to, screws, nuts and bolts, rivets, snap-fits, tacks, nails, loop fasteners, and interlocking male/female connectors, such as fishhook connectors, a fish hook connector includes a male portion with a protrusion on its circumference. Inserting the male portion into the female portion substantially permanently locks the two portions together.

As used herein, the term "couple" includes, but is not limited to, joining, connecting, fastening, linking, or associating two things integrally or interstitially together.

As used herein, the term "configure" or "configuration" means to design, arrange, set up, or shape with a view to specific applications or uses. For example: a military vehicle that was configured for rough terrain; configured the computer by setting the system's parameters.

As used herein, the term "substantially" refers to something which is done to a great extent or degree; a significant or great amount; for example, as used herein "substantially" as applied to "substantially" covered means that a thing is at least 90% covered.

As used herein, the term "alignment" refers to the spatial property possessed by an arrangement or position of things in a straight line or in parallel lines.

As used herein, the terms "orientation" or "position" used interchangeably herein refer to the spatial property of a place where or way in which something is situated; for example, "the position of the hands on the clock."

As used herein, the term "about" refers to an amount that is plus or minus 10 percent of a stated or implied range.

As used herein, the term "resilient" and "resiliency" refers to the physical property of an object and/or a material that can return to its original shape or position after deformation that does not exceed its elastic limit.

These terms may be defined with additional language in the remaining portions of the specification.

SUMMARY OF THE INVENTION

The present invention is directed to eyewear for protecting a user's eyes. The eyewear includes at least one lens, a frame portion coupled to at least a portion of an outer edge of the lens, and a pair of ear pieces coupled to a portion of the eyewear. The lens has at least one first portion positioned adjacent the user's nose and at least one second portion which is positioned adjacent an outer edge of the user's eye when the eyewear is positioned on the user's face. The lens is positioned to extend a distance from the user's eye and covers the user's eye from the distance. Additionally, the lens includes an opening positioned in the lens, where the opening has an air permeable covering to provide protection, promote airflow and reduce fogging.

The present invention is also directed to eyewear that includes a pair of lenses and a frame connected to at least a portion of an outer edge of each lens. There is no connection between one lens and the other lens positioned across the user's nose. Additionally, the frame includes at least one ear piece that extends from one lens and around the back of the user's head to an opposite lens such that the frame does not extend across the user's nose.

Additionally, the present invention is also directed to eyewear including at least one lens, a frame coupled to at least a portion of an outer edge of the lens, and a pair of ear pieces. The lens has a generally convex configuration and an outer edge which includes an upper edge and a lower edge. The frame is positioned along the upper edge and includes a filtering/absorbent portion positioned between the frame and the user's forehead. The frame and filtering/absorbent portion cooperate to substantially seal the upper edge of the eyewear to the user's face.

The present invention is also directed to eyewear including a least one lens, a frame coupled to at least a portion of an outer edge of the lens, and a pair of ear pieces. Additionally, the lens has an outer edge which includes an upper edge and a lower edge. The frame is coupled to at least a portion of the outer edge of the lens and includes an upper frame, having at least one area for attaching a forehead pad, and a lower frame positioned adjacent a lower edge of the lens. The lower frame has at least one opening configured to receive an air permeable cartridge.

Finally, the present invention is also directed to eyewear including at least one lens and at least one frame portion coupled to at least a portion of the upper edge of the lens. The lens has at least one first portion positioned adjacent the user's nose and at least one second portion which is positioned adjacent an outer edge of the user's eye when the eyewear is positioned on the user's face. The lens extends a distance from the user's eye and covers the user's eye from the distance. Also, the lens has an outer edge including an upper edge. The frame portion includes a pair of ear pieces and at least a portion of the frame portion and ear pieces includes a tubular conduit. A plurality of air openings are formed in the conduit and at least one roller is moveably positioned in the conduit such that movement of the user's head causes movement of the roller. As the roller moves, it pushes air through the conduit and out of at least one of the plurality of openings to reduce fogging of the lens.

BRIEF DESCRIPTION OF THE DRAWINGS

FIG. 1 is a side view of the eyewear of the present invention, showing a common lens extending across a user's eyes and vent portion positioned in the lens adjacent to provide air flow adjacent an outer periphery of the lens and an outer edge of a user's eyes;

FIG. 2 is a perspective view of the eyewear of FIG. 1;

FIG. 3 is a side view of another embodiment of eyewear of the present invention, showing eyewear having a pair of lenses which do not interconnect over a user's nose, but instead have an ear piece which extends from one lens around an outer circumference of a user's head to another lens;

FIG. 4 is a perspective view of the eyewear of FIG. 3;

FIG. 5 is a top plan view of the eyewear of FIGS. 3 and 4;

FIG. 6 is a side view of yet another embodiment of eyewear of the present invention, showing eyewear having a single lens which curves or bubbles outward away from a user's eyes, and which is designed to fit against a user's face, that is, a user's forehead, cheeks and nose, the eyewear having a pad positioned against a user's forehead to permit air flow to a user's eyes and to assist in reducing moisture adjacent a user's eyes;

FIG. 7 is a perspective view of the eyewear of FIG. 6;

FIG. 8 is a top plan view of the pad of the eyewear of FIG. 7 designed to fit between the eyewear and a user's forehead;

FIG. 9 is a side view of still yet another embodiment of eyewear of the present invention, showing eyewear having a single lens which includes an upper and lower frame, the upper frame configured to dispose a pad against a user's forehead and the lower frame having a removable cartridge for reducing moisture adjacent a user's eyes and face;

FIG. 10 is a perspective view of the eyewear of FIG. 9;

FIG. 11 is a partial view of a portion of the lower frame of the eyewear of FIGS. 9 and 10, showing the portion of the lower frame coupled to an outer edge of the lens;

FIG. 12 is a partial view of a portion of the lower frame of FIGS. 9 and 10, showing an opening in the portion of the lower frame configured to hold a removable cartridge to permit air flow and wicking of moisture away from a user's eyes and face;

FIG. 13 is a side view of another embodiment of eyewear of the present invention, showing eyewear having a single lens which includes a hollow tubular frame configured to hold at least one roller, the frame including an air intake opening in at least one ear piece and the frame including a plurality of openings adjacent a user's eyes which are covered by a flapper valve, such that movement of a user's head results in the roller pushing air out of the plurality of openings and through the flapper valve to provide air flow to a user's eyes and face;

FIG. 14 is a perspective view of the eyewear of FIG. 13; and

FIG. 15 is a partial view of the frame of FIGS. 13 and 14, showing a roller (in phantom lines) and the movement of one flapper valve away from the plurality of openings to provide air to a user's eyes and face.

DETAILED DESCRIPTION

Reference will now be made in detail to one or more embodiments of the invention, examples of which are illustrated in the drawings. Each example and embodiment is provided by way of explanation of the invention, and is not meant as a limitation of the invention. For example, features illustrated or described as part of one embodiment may be used with another embodiment to yield still a further embodiment. It is intended that the invention include these and other modifications and variations as coming within the scope and spirit of the invention.

Safety glasses and/or glasses used in sports applications are usually made with shatter-resistant plastic lenses to protect the eye. Although safety lenses may be constructed from a variety of materials that vary in impact resistance, certain standards suggest that they maintain a minimum 1 millimeter thickness at the thinnest point, regardless of material. Safety glasses can vary in the level of protection that they provide based on their intended application. For example, those used in medicine may be expected to protect against blood splatter while safety glasses in a factory might have stronger lenses and a stronger frame and may include additional shields or safety features. The lenses of safety glasses may be shaped for correction or magnification. Some safety glasses may also be designed to fit over corrective glasses or sunglasses.

While face shields, goggles, and so forth are available as well, some studies have suggested that they will not always be used due to their bulkiness and weight. Therefore, lighter weight eyewear, while not providing as much protection as full face shields and/or goggles, may be preferred and actually worn more frequently by users due to their lack of size or bulk and their reduced weight. In addition, recent studies have also suggested that when safety glasses are both light weight and have a more stylish design, these features in combination also result in a higher usage of safety glasses in the appropriate situations.

The lenses of safety glasses are desirably made from plastic. There are a number of suitable plastics which may be utilized. Examples of some plastics used for eyewear include polycarbonates, such as LEXAN® manufactured by General Electric, Fairfield, Conn., allyl diglycol polycarbonate such as CR-39® manufactured by PPG Industries, Pittsburgh, Pa., and thermoplastic elastomers (TPE) such as Kraton® or Dynaflex® produced by GLS, McHenry, Ill.

Other materials may also be available for making lenses; other materials may be added to or provided via, for example, but not by way of limitation, a coating, cover, and so forth provided to the lenses to provide additional features. Such features may include, but are not limited to ultraviolet (UV) light protection, anti-fogging protection, anti-reflective (AR) protection, and so forth. Safety and/or sports glasses may desirably be ranked according to meeting certain requirements. In the United States, the American National Standards Institute (ANSI) has various standards and ratings for safety glasses. Safety glasses may be rated according to their ability to resist, for example, flying debris, heat, sparks, acid splash, abrasive blasting materials, glare, radiation, and so forth.

Safety and/or sports glasses may have numerous uses in a household situation. Safety glasses may be used while painting, while cutting grass, and so forth. Many different types of sports have found protective eyewear useful as well. Safety glasses or eyewear are increasingly needed for new industrial, home and sports applications.

Referring now to FIGS. 1-15 in general, and FIGS. 1 and 2 in particular, the present invention provides eyewear adapted to protect a user's eyes. In the present embodiment, the eyewear 10 includes at least one lens 12. The lens may include a single lens 12 which extends generally across a user's face 14 and specifically across a user's nose 16 to cover both eyes 18 and thereby to provide protection to both eyes 18.

Desirably the lens 12 extends a distance 20 from the user's eyes and is configured to cover or extend over each of a user' eyes 18 from the distance 20 to provide protection thereto. The lens 12 desirably includes at least one, and in this embodiment a pair of first portions 22 which are positioned adjacent a user's nose 16. The lens 12 desirably also includes a pair of second portions 24 which are positioned adjacent an outer edge 25 of a user's eye 18. The lens 12 includes a connector 26 which is positioned across a user's nose 16. The lens 12 may include a frame 27 positioned about at least a portion of an outer edge 29 of the lens 12.

A pair of ear pieces 28 are desirably coupled to the frame 27 and/or lens 12; in this instance, each ear piece 28 is coupled to a portion of the frame 27. Each ear piece 28 is configured to hold the lens 12 adjacent a user's face 14. Desirably, each ear piece 28 includes a first end 32 and a second end 34. A temple piece 35 desirably extends between the first end 32 and the second end 34.

The first end 32 of each ear piece 28 is desirably pivotably coupled near the second portions 24 of the lens 12. The second end 34 desirably is positioned over and/or around a portion of a user's ear 36 when the eyewear 10 is being worn. Similarly, the temple piece 35 is desirably configured to be positioned adjacent a user's temple 38.

The lens 12 includes an air permeable covering or vent portion 40 provided in the second portions 24 of the lens 12. Desirably, the second portions 24 include openings (not shown) in the lens 12 which are covered by mesh woven wire and/or plastic woven material which provides at least a portion of the vent portion 40. Such a vent portion 40 may be removable and/or interchangeable, and be snapped in and out of the lens via a tongue and groove connection (not shown), and so forth. The vent portion 40 permits air to flow into and away from a user's face 14, but reduces or prevents undesirably matter, whether, gaseous, liquid or solid, from entering the vent portion 40. The vent portion 40 may include a removable desiccant cartridge and/or superabsorbent material as well (such a desiccant cartridge is shown in FIGS. 10 and 12). The vent portion 40 may include additional materials as well.

A nose piece 42 may be coupled to a portion of the frame 27 and/or the lens 12. The nose piece 42 may spaced the lens 12 a distance from a user's face 14 to promote air flow through the vent portions 40.

In an alternative embodiment, it will be appreciated that the lens 12 may be provided as a pair of lenses, with one lens extending over one of each of the eyes of a user when the eyewear is positioned on a user's face (not shown). In such an embodiment, a nose piece will desirably be provided to assist in holding the lenses to a user's face (not shown). The eyewear may be provided without a frame, and in such an instance, the ear pieces will be coupled to the lens or lenses (not shown).

In another embodiment of the invention, the eyewear 110 shown in FIGS. 3-5 is similar to the eyewear 10 shown in FIGS. 1 and 2 and described in detail previously herein, except that the eyewear 110 has features which differ from those of eyewear 10. In the present embodiment, the eyewear 110 includes at least a pair of lenses 112.

Desirably each lens 112 extends a distance 120 from the user's eyes 18 and is configured to cover or extend over each of a user' eyes 18 from a distance 120 to provide protection thereto, as illustrated in FIGS. 3 and 4. Each lens 112 desirably includes a first portion 122 which is positioned near a user's nose 16 and a second portion 124 which is positioned adjacent an outer edge 25 of a user's eye 18. Notably, there is no connection of the lenses 112 across a user's nose 16. The lens 112 may include a frame 126 positioned about at least a portion of an outer edge 127 of the lens 112.

While the inventors do not wish to be limited by a particular theory and/or embodiment, thermal images reveal that the hottest part of a user's face is over the bridge of a user's nose 16. Therefore, rather than to change a nose piece on eyewear, the nose piece has been eliminated in the present eyewear 112. The bridgeless design opens up this area of a user's face to direct ventilation and provides a user's exhalent with a vertical flow path or "chimney" between the lenses, which prevents any heat build up, since no nose piece is in its path to receive the heat and/or moisture.

An ear piece 128 having a first end 132 and a second end 134 is coupled to the lenses 112 via the frame 126. An elongated portion 136 extends between the first end 132 and the second end 134. Specifically, the first end 132 may be coupled to the frame 126 adjacent the second portion 124 of one lens 112. The elongated portion 136 is configured to follow and extend about on outer circumference 44 of a user's head 46. The second end 134 is desirably coupled to the opposite lens 112 via the frame 126. It will be appreciated that the ear piece 128 may be coupled to each lens 112 rather than the frame 126 (not shown). The elongated portion 136 may include one or a plurality of adjustors 138 which permit the elongated portion 136 to be custom fit to the outer circumference 44 of a user's head 46, as shown in FIGS. 4 and 5. The adjustors 138 may be, for example, but not by way of limitation overlapped, sliding, telescoping, and so forth, so that the ear piece 128 may assist in holding the lenses 112 to a user's face 14. That is, the adjustors 138 permit the elongated portion 136 to be lengthened or shortened so that the ear piece 128 substantially conforms to a portion of an outer circumference 44 of a user's head 46.

In addition, the each first and second ends 132, 134 may be movably coupled to each lens 112. That is, each lens 112 may be pivotably coupled to the ear piece 128 via hinges, and so forth. Alternatively, the ear piece 128 may be fixedly coupled to each lens 126. Desirably, the frame 126 and/or ear piece 128 may be formed from a resilient material.

Desirably, each lens 112 or a portion of the frame 126 includes a nose piece 140 which is positioned on only one side 48 of a user's nose 16. The resulting eyewear 110 which is not coupled together across a user's nose 16 permits heated, moist air to be expelled upward and/or outward, away from a user's eyes 18, thereby reducing or preventing heat and/or moist exhaled air from a user's nose 16 from fogging the lenses 112 and permitting the heat and moisture therein to be expelled away from the lenses 112.

In addition, the eyewear 110 is configured to permit some air to flow under each lens 112 adjacent each second portion 124 of each lens 112. This air flow may be permitted or eliminated via the adjustment of each lens 112 and/or ear piece 128.

In an alternative embodiment, it will be appreciated that the pair of lenses 112 may be provided without a frame 126 (not shown). In such an embodiment, the ends 132, 134 of the ear piece 128 will couple directly to a portion of a lens 112 (not shown). In addition, a nose piece may be provided which releasably couples to one or more of the lenses 112 and/or frame 126 (not shown).

In another embodiment of the invention, the eyewear 210 shown in FIGS. 6-8 is similar to the eyewear 10, 110 shown in FIGS. 1-5 and described in detail previously herein, except that the eyewear 210 has features which differ from those of eyewear 10 and 110. In the present embodiment, the eyewear 210 includes at least one lens 212, as shown in FIGS. 6 and 7. The lens 212 desirably includes a single lens 212 which bubbles outward away from a user's eyes 18 and extends generally across a user's face 14 and specifically across a user's nose 16 to cover both eyes 18 and thereby to provide protection to both eyes 18. The eyewear 210 is similar to goggles, but it has additional features which permit airflow and/or moisture absorption. In addition, the eyewear 210 provides a significantly larger "microenvironment" that, due to it's size and configuration, is less susceptible to small changes in temperature or moisture that may cause fogging and/or discomfort. That is, it takes a greater amount of heat and moisture to effect this larger area, which is an advantage when wearing the eyewear 210 for a period of time. In addition, the open area around a bridge of a user's nose 16 assists in diminishing the one potential hotspot in the area of the microenvironment.

Desirably the lens 212 extends a distance 220 from the user's eyes 18 and is configured to cover or extend over each of a user' eyes 18 from the distance 220 to provide protection thereto. The outer surface 221 of the lens is desirably somewhat convex to curve outward, away from a user's eyes 18. The lens 212 desirably includes at least one, and in this embodiment a pair of first portions 222 which are positioned adjacent a user's nose 16. The lens 212 desirably also includes a pair of second portions 224 which are positioned adjacent an outer edge 25 of a user's eye 18. The lens 212 also desirably includes a connector 226 which is positioned across a user's nose 16. The lens 212 may include a frame 230 positioned about at least a portion of an outer edge 227 of the lens 212.

A pair of ear pieces 228 are desirably coupled to the frame 230. In this instance, the frame 230 is provided primarily, but not by way of limitation, along an upper edge of the lens 212. Alternatively, the ear pieces 228 may be coupled to the lens 212 (not shown).

In this instance, each ear piece 228 desirably includes a first end 232 and a second end 234. A temple piece 235 desirably extends between the first end 232 and the second end 234. The first end 232 of each ear piece 228 may be pivotably coupled near the second portions 224 of the lens 212. The second end 234 desirably is positioned over and/or around a portion of a user's ear 16 when the eyewear 210 is being worn. Similarly, the temple piece 235 is desirably configured to be positioned adjacent a user's temple 38. It will be understood that the ear pieces 228 may be fixed, hingeably coupled to the frame, and so forth.

The eyewear 210 includes a filtering/absorbent portion 240 provided adjacent the frame 230. It is desirably positioned along an upper edge of the frame 230. The filtering/absorbent portion 240 may include a honeycomb-type elastic material which permits air flow to a user's eyes 18 but is positioned against a user's forehead 50, as shown in FIGS. 7 and 8. The filtering/absorbent portion 240 may be constructed from any material or combination of materials which permits air flow to a user's eyes, but limits or prevents the admission of liquids and/or solids therethrough. Therefore, the filtering/absorbent portion 240 may appear as a more solid-type of material such as the portion 240 illustrated in FIG. 6. One such material may include, for example, open cell foam rubber. Other materials may include removable pads which provide the filtering/absorbent portion 240. Such materials may include, but not by way of limitation, desiccants and/or superabsorbents materials. Such removable pads may be releasably coupled to the upper edge of the frame 230 and/or lens 212 (not shown). Such releasable coupling may be accomplished by the use of pressure sensitive adhesive, cohesive adhesive, hook and loop material, and so forth. In addition, or instead of, such a pad may include one or more of superabsorbent materials, desiccants, and so forth.

A nose piece 244 may be coupled to a portion of the lens 212 or the frame 230. The nose piece 244 as well as the lens 214 and frame 230 desirably holds the eyewear 212 closely and/or snuggly against a user's face nose 16, cheeks 52 and face 14 such that a microenvironment is provided and the primary air flow to a user's eyes 18 is through the filtering/absorbent portion 240. The filtering/absorbent portion 240 provides filtered air and wicks moisture away from a user's eyes 18.

The lens 212, frame 230, ear pieces 228, and so forth my be constructed partially or totally from a resilient material, which provides comfort and a custom fit or seal against a user's face 18. In addition the convex outer surface 221 of the lens curves outward and peripherally away from a user's eyes 18 to provide significant coverage while permitting excellent vertical, horizontal and peripheral visibility. One or more filtering absorbent portions may be used along any portion(s) of the eyewear.

In an alternative embodiment, it will be appreciated that the lens 212 may be provided as a pair of lenses, with one lens extending over one of each of the eyes of a user when the eyewear is positioned on a user's face (not shown). In such an embodiment, a nose piece will desirably be provided to assist in holding the lenses together adjacent a user's face (not shown). The eyewear may be provided without a frame, and in such an instance, the ear pieces will be coupled to the lens or lenses (not shown) and the filtering/absorbent pad and/or cartridge will be coupled to an upper edge of the lens or lenses (not shown).

In another embodiment of the invention, the eyewear 310 shown in FIGS. 9-12 is similar to the eyewear 10, 110 and 210 shown in FIGS. 1-8 and described in detail previously herein, except that the eyewear 310 has features which differ from those of eyewear 10, 110 and 210. In the present embodiment, the eyewear 310 includes at least one lens 312, as illustrated in FIGS. 1 and 2. The lens 312 may include a single lens 113 which extends generally across a user's face 14 and specifically across a user's nose 16 to cover both eyes 18 and thereby to provide protection to both eyes 18.

Desirably the lens 312 extends a distance 320 from the user's eyes and is configured to cover or extend over each of a user' eyes 18 from the distance 320 to provide protection thereto. The lens 312 desirably includes at least one, and in this embodiment a pair of first portions 322 which are positioned adjacent a user's nose 16. The lens 312 desirably also includes a pair of second portions 324 which are positioned adjacent an outer edge 25 of a user's eye 18. The lens 312 includes a connector 326 which is positioned across a user's nose 16. The lens 312 may include a frame 330 positioned about at least a portion of an outer edge 327 of the lens 312.

In this embodiment, the frame 330 includes an upper frame 340 which extends along an upper edge of the lens 312 and a lower frame 350 which extends along a lower edge of the lens 312. It will be understood, however, that the frame 330 may also extend completely around the lens or partially about the lens.

A pair of ear pieces 328 are desirably coupled to the frame 330, although it will be appreciated that the ear pieces 328 may be coupled to the lens 312 instead (not shown). In this instance, each ear piece 328 desirably includes a first end 332 and a second end 334. A temple piece 335 desirably extends between the first end 332 and the second end 334. The first end 332 of each ear piece 328 may be pivotably coupled near the second portions 324 of the lens 312. The second end 334 desirably is positioned over and/or around a portion of a user's ear 16 when the eyewear 310 is being worn. Similarly, the temple piece 335 is desirably configured to be positioned adjacent a user's temple 38.

A filtering/absorbent pad 360 is provided adjacent the upper frame 340, and is positioned on an inner edge of the frame 330 against a user's forehead 50. The filtering/absorbent pad 360 may include an absorbent material and/or a desiccant which permits moisture from the air adjacent a user's eyes 18 and face 14 to be absorbed. The filtering/absorbent pad 360 may be constructed from any material or combination of materials which permits air flow and/or moisture control, but limits or prevents the admission of liquids and/or solids therethrough. One such material may include, for example, open cell foam rubber. Other materials may include one or more of superabsorbent materials, desiccants, and so forth. The pad 360 is desirably a removable pad which is releasably coupled to the upper frame 340. Such releasable coupling may be accomplished by, for example, but not by way of limitation, the use of pressure sensitive adhesive, cohesive adhesive, hook and loop material, and so forth.

The lower frame 350 may include an L-shaped flange 364 which is desirably is made from a resilient, flexible material such that the lower frame 350 conforms to the nose 16, cheeks 52 and face 14 of a user. As shown in FIG. 11, the L-shaped flange 364 may provide a groove into which the outer edge 327 of the lens 312 couples. This configuration may permit the lower frame 350 to be releasably coupled to the lens 312. The L-shaped flange 364 may be configured to have an opening 366 therein which is sized to permit an air permeable disposable cartridge 368 to be disposed therein, as illustrated in FIGS. 10 and 12.

The cartridge 368 desirably includes a material which permits air to flow to a user's eyes 18, but absorbs moisture. Such a cartridge 368 may include a super absorbent material, desiccant(s), and so forth. The cartridge 368 may be disposable as well. The cartridge 368 may be formed to snap into the opening 366, or may be coupled to the L-shaped flange 364 by any method described herein or known in the art.

Desirably, the lower frame 350 provides a custom fit to a user's face 14. The outer edge 327 of the lens 312 adjacent the second portions 324 of the lens 312 between the upper frame 340 and the lower frame 350 may provide a space for air to flow to a user's eyes 18. The pad 360 and the cartridge 368 cooperate with a fog-resistance coating applied to the lens 312 to prevent fogging of the lens 312 while permitting air flow to a user's eyes 18.

In an alternative embodiment, it will be appreciated that the lens 312 may be provided as a pair of lenses, with one lens extending over one of each of the eyes of a user when the eyewear is positioned on a user's face (not shown). In such an embodiment, a nose piece will desirably be provided to assist in holding the lenses together adjacent a user's face (not shown). The eyewear may be provided without a frame, and in such an instance, the ear pieces desirably couple to the lens or lenses (not shown) and the filtering/absorbent pad and cartridge will be coupled to an upper edge of the lens or lenses (not shown). Further, the ear pieces may hingeably couple to the frame and/or lens(es) (not shown).

In another embodiment of the invention, the eyewear 410 shown in FIGS. 13-15 is similar to the eyewear 10, 110, 210 and 310 shown in FIGS. 1-12 and described in detail previously herein, except that the eyewear 410 has features which differ from those of eyewear 10, 110, 210 and 310. In the present embodiment, the eyewear 410 includes at least one lens 412, as illustrated in FIGS. 1 and 2. The lens 412 may include a single lens 412 which extends generally across a user's face 14 and specifically across a user's nose 16 to cover both eyes 18 and thereby to provide protection to both eyes 18.

Desirably the lens 412 extends a distance 420 from the user's eyes and is configured to cover or extend over each of a user' eyes 18 from the distance 420 to provide protection thereto. The lens 412 desirably includes at least one, and in this embodiment a pair of first portions 422 which are positioned adjacent a user's nose 16. The lens 412 desirably also includes a pair of second portions 424 which are positioned adjacent an outer edge 25 of a user's eye 18. The lens 412 includes a connector 426 which is positioned across a user's nose 16. The lens 412 may include a frame 430 positioned about at least a portion of an outer edge 427 of the lens 412.

In this embodiment, the frame 430 is positioned along an upper edge 438 of the lens 412. It will be understood, however, that the frame 430 may also extend completely around the lens or partially about the lens (not shown).

A pair of ear pieces 428 are desirably formed integrally with the frame 430, although it will be appreciated that the ear pieces could be coupled to the lens 412 instead (not shown). In this instance, each ear piece 428 desirably includes a first end 432 provided adjacent the second portion 424 of the lens 412 and a second end 434. A temple piece 435 desirably extends between the first end 432 and the second end 434. The second end 434 desirably is positioned over and/or around a portion of a user's ear 16 when the eyewear 410 is being worn. Similarly, the temple piece 435 is desirably configured to be positioned adjacent a user's temple 38. It will be understood that the ear pieces 428 may be fixed, telescoping and/or pivotable (not shown).

In the present embodiment, the frame 430 and the ear pieces 428 are formed to provide a conduit 440. The conduit 440 has generally, but not by way of limitation, circular or round inner diameter which provides a tubular conduit. The conduit 440 is closed at each second end 434 of each ear piece 428. At least one generally round roller 442 is positioned inside of the conduit 440, and the roller 442 is desirably sized and configured to move freely through the length of the conduit 440. The conduit 440 includes an air intake area 444 positioned at either second end 434 of the ear pieces 328. In addition, as shown in FIG. 15, at least one, and desirably, a plurality of openings 446 are positioned in the conduit 440, desirably adjacent a user's eyes. Each of the plurality of openings 446 may be covered by a diaphragm-style flapper valve 448 positioned over the openings 446. In this manner, the "microenvironment" created in the distance 420 between a user's eyes 18 and the eyewear 410 is provided additional yet protected air flow. The motion of a user's head may be used to kinetically drive airflow from the air intake area 444 through the plurality of openings 446 and valves 448. That is, movement of a user's head causes the at least one roller 442 to move through the conduit 440, pushing air therethrough, which exits through the plurality of openings 446 and valves 448.

It will be appreciated that the features and/or components of one embodiment may be combined, in whole or in part, with another embodiment. In some instances, the combination may provide another, different embodiment.

In addition, but not by way of limitation, one or each of the pair of ear pieces shown and/or described herein may be hingeably coupled to the lens and/or frame; alternatively, one or each may be pivotably coupled thereto, or may be telescoping. In addition, one or each of the pair of ear pieces may be fixed and relatively unmovable.

It will be appreciated that the features and/or components of one embodiment may be combined, in whole or in part, with another embodiment. In some circumstances, such combination may yield yet another embodiment.

While the present invention has been described in connection with certain preferred embodiments, it is to be understood that the subject matter encompassed by way of the present invention is not to be limited to those specific embodiments. On the contrary, it will be appreciated that some elements and/or articles may be used with other elements or articles. It is intended for the subject matter of the invention to include all alternatives, modifications and equivalents as can be included within the spirit and scope of the invention.

What is claimed is:

1. Eyewear adapted to protect a user's eyes, the eyewear comprising:

at least one lens, the lens having at least one first portion positioned adjacent a user's nose and at least one second portion which is positioned adjacent an outer edge of a user's eye when the eyewear is positioned on a user's face, the lens positioned to extend a distance from a user's eye and the lens configured to cover a user's eye from the distance, the lens having an outer edge including an upper edge; and at least one frame portion coupled to at least a portion of the upper edge of the lens, the frame portion including a pair of ear pieces and at least a portion of the frame portion and ear pieces including a tubular conduit, a plurality of air openings formed in the conduit and at least one roller moveably positioned in the conduit such that movement of a user's head causes movement of the roller, and as the roller moves it pushes air through the conduit and out of at least one of the plurality of openings to reduce fogging of the lens.

2. The eyewear of claim 1, wherein the at least one lens further comprises a common lens which extends over both of a user's eyes when the eyewear is positioned on a user's face.

3. The eyewear of claim 1, wherein the plurality of air openings are covered by at least one diaphragm flapper valve provided on the outside of the conduit.

4. The eyewear of claim 3, wherein each ear piece includes a first portion and a second portion at an opposite end thereof, and wherein the first portion is coupled to the frame portion and the conduit extends into the first portion of each air piece and at least a portion of the second portion of each ear piece.

5. The eyewear of claim 4, wherein air intake into the conduit is provided via an opening in the second portion of at least one of the ear pieces.

6. The eyewear of claim 5, wherein air enters the conduit via the opening in the second portion of at least one of the ear pieces and air is moved via the roller in the conduit such that the air is expelled adjacent a user's eyes via the plurality of openings and the diaphragm flapper valve adjacent a user's eyes.

* * * * *